(12) United States Patent
Iida et al.

(10) Patent No.: US 11,590,481 B2
(45) Date of Patent: Feb. 28, 2023

(54) HETEROATOM-DOPED ZEOLITES FOR BIFUNCTIONAL CATALYTIC APPLICATIONS

(71) Applicant: ExxonMobil Technology and Engineering Company, Annandale, NJ (US)

(72) Inventors: Takayuki Iida, Jersey City, NJ (US); Jihad M. Dakka, Whitehouse Station, NJ (US); Brandon M. Carcuffe, Hackettstown, NJ (US); Aaron Peters, New Hope, PA (US)

(73) Assignee: ExxonMobil Technology & Engineering Company, Annandale, NJ (US)

( * ) Notice: Subject to any disclaimer, the term of this patent is extended or adjusted under 35 U.S.C. 154(b) by 0 days.

(21) Appl. No.: 17/349,989

(22) Filed: Jun. 17, 2021

(65) Prior Publication Data
US 2022/0401935 A1  Dec. 22, 2022

(51) Int. Cl.
*B01J 29/74* (2006.01)
*C07C 5/27* (2006.01)
*C10G 45/64* (2006.01)
*B01J 37/04* (2006.01)
*B01J 37/00* (2006.01)
(Continued)

(52) U.S. Cl.
CPC ....... *B01J 29/7415* (2013.01); *B01J 37/0009* (2013.01); *B01J 37/009* (2013.01); *B01J 37/04* (2013.01); *B01J 37/082* (2013.01); *B01J 37/30* (2013.01); *C07C 5/2737* (2013.01); *C10G 45/64* (2013.01); *B01J* 2229/183 (2013.01); *C07C 2529/74* (2013.01); *C10G 2300/305* (2013.01); *C10G 2300/4018* (2013.01)

(58) Field of Classification Search
None
See application file for complete search history.

(56) References Cited

U.S. PATENT DOCUMENTS

| 3,308,069 A | 3/1967 | Wadlinger et al. |
| RE28,341 E | 2/1975 | Wadlinger et al. |

(Continued)

FOREIGN PATENT DOCUMENTS

| WO | 2016/126431 A1 | 8/2016 |
| WO | 2018/160327 A1 | 9/2018 |

OTHER PUBLICATIONS

Hidalgo, J. et al., Current uses and trends in catalytic isomerization, alkylation and etherification process to improve gasoline quality, Cent Eur J. Chem. 12(1), pp. 1-13, 2014.
(Continued)

*Primary Examiner* — Renee Robinson
*Assistant Examiner* — Alyssa L Cepluch

(57) ABSTRACT

Provided herein are methods for hydroisomerization of a hydrocarbon feedstock comprising contacting the hydrocarbon feedstock with hydrogen and a catalyst to yield a hydrocarbon product having an increase in branched hydrocarbons relative to the hydrocarbon feedstock. The present catalysts comprise a heteroatom-doped Beta zeolite having a trivalent cation as a framework metal oxide, an extra-framework species comprised of cerium and/or cobalt, and from 0.01 to 1.5 wt. % of a group VIII or VIB metal, or a combination thereof.

10 Claims, 4 Drawing Sheets

(51) Int. Cl.
*B01J 37/30* (2006.01)
*B01J 37/08* (2006.01)

(56) References Cited

U.S. PATENT DOCUMENTS

| | | | | |
|---|---|---|---|---|
| 5,055,629 | A | * | 10/1991 | Gilson .................. C07C 5/2791 585/739 |
| 6,080,904 | A | | 6/2000 | Chang et al. |
| 6,124,232 | A | | 9/2000 | Chang et al. |
| 2005/0277800 | A1 | * | 12/2005 | Sugi ...................... C07C 5/2775 502/64 |
| 2010/0322847 | A1 | * | 12/2010 | Xiao ...................... C10G 11/05 423/709 |
| 2013/0324782 | A1 | | 12/2013 | Shakun et al. |
| 2014/0275689 | A1 | | 9/2014 | Petrovic |
| 2015/0273450 | A1 | | 10/2015 | Lai |

OTHER PUBLICATIONS

Izutsu, Y. et al., Synthesis and Characterization of Chromium-Added Pt/Beta Zeolites and its Catalytic Performance of n-Heptane Isomerization, Catal. Lett., 143, pp. 486-494, 2013.

Liu, P. et al., Rare Earth Metals Ion-exchanged β-zeolites as Supports of Platinum Catalysts for Hydroisomerization of n-heptane, Chin. J. Chem. Eng., 19, pp. 278-284, 2011.

Ushiki, R. et al., Co-loading of Pt and Fe on *BEA Zeolite for Enhanced Isomerization Selectivity in n-Heptane Conversion, Chem Lett. 47, pp. 1428-1430, 2018.

Walter, D., Primary Particles—Agglomerates—Aggregates, in Nanomaterials, Deutsche Forschungsgemeinschaft (DFG), Wiley, pp. 1-24, 2013.

Wang, Z.B. et al., Isomerization of n-heptane over Pt-loaded zeolite β catalysts, Applied Catalysis A: General, 159, pp. 119-132, 1997.

Zhang, X. et al., Synthesis and Catalytic Performance of the Framework-Substituted Manganese β zeolite, Catal Lett, 137, pp. 210-215, 2010.

* cited by examiner ns at 250° C. and LHSV equal to 3, 6

HETEROATOM-DOPED ZEOLITES FOR BIFUNCTIONAL CATALYTIC APPLICATIONS

FIELD

The present disclosure relates to hydroisomerization of light paraffins and more specifically relates to novel catalysts for performing the same.

BACKGROUND

Hydroisomerization of light linear paraffins is a primary reaction for utilization of certain oil resources in order to boost octane values in a gasoline fuel product. Zeolite catalyst have been employed for this purpose. However, light paraffin hydroisomerization catalysts based on zeolites can suffer from side reactions known as cracking. Metal oxide catalysts have been developed for use in these reactions as metal oxide catalysts have high activity and selectivity for hydroisomerization of light linear paraffins. However, the presence of poisons such as S, N, $H_2O$, and Cl can diminish the activity of the catalyst.

SUMMARY

Provided herein are methods for hydroisomerization of a hydrocarbon feedstock comprising contacting the hydrocarbon feedstock with hydrogen and a catalyst to yield a hydrocarbon product having an increase in branched hydrocarbons relative to the hydrocarbon feedstock. The present catalysts comprise a heteroatom-doped Beta zeolite comprising trivalent cation as a framework metal oxide, an extra-framework species comprised of cerium and/or cobalt, and from 0.01 to 1.5 wt. % of a group VIII or VIB metal, or a combination thereof.

Also provided herein are methods of synthesizing a heteroatom doped-Beta zeolite comprising cerium or cobalt as an extra-framework species. The method comprises crystalizing a reaction mixture comprising water, $SiO_2$, and a framework metal oxide. The reaction mixture comprises a molar ratio of structure directing agent cation, Q, to $SiO_2$ in the reaction mixture of 0 to 4; a molar ratio of $SiO_2$ to framework metal oxide in said reaction mixture of greater than 10; a molar ratio of water to $SiO_2$ in the reaction mixture of greater than 0; a molar ratio of alkali metal M to $SiO_2$ in the reaction mixture of from 0.1 to 1; and a molar ratio of $SiO_2$ to Al source in the reaction mixture of greater than 5. The present methods of synthesizing the heteroatom doped-Beta zeolite include the step of calcining the heteroatom-doped Beta zeolite wherein framework heteroatoms are converted into extra-framework species at a temperature from 100° C. to 800° C., under inert, oxidative and/or steaming conditions. The reaction mixture can further comprise a mineralizer and/or a structure directing agent.

These and other features and attributes of the disclosed methods and compositions of the present disclosure and their advantageous applications and/or uses will be apparent from the detailed description which follows.

BRIEF DESCRIPTION OF THE DRAWINGS

To assist those of ordinary skill in the relevant art in making and using the subject matter hereof, reference is made to the appended drawings, wherein.

DETAILED DESCRIPTION

Figure 1:
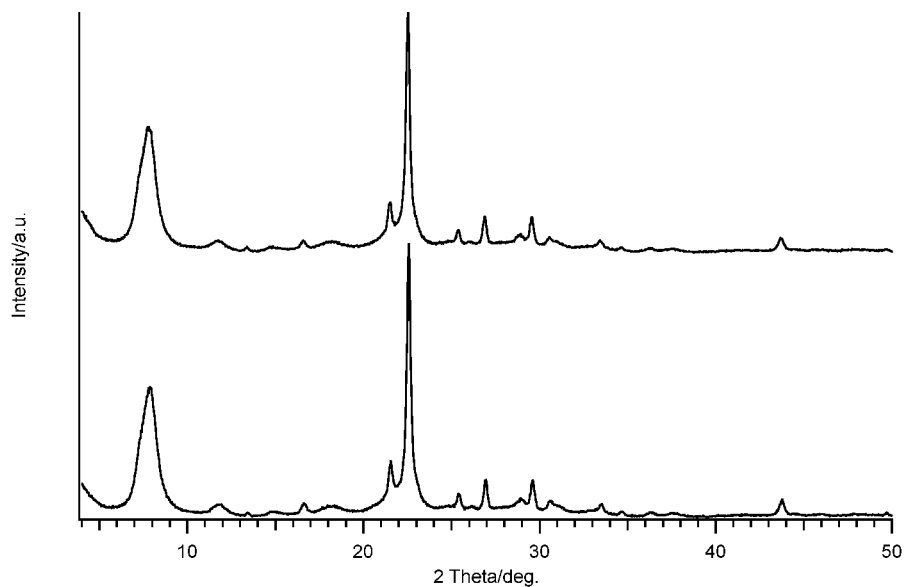
FIG. 1 is a graph of the x-ray diffraction of Ce-doped Al-Beta zeolite (top line) versus Al-Beta zeolite (bottom line).

As used in the present disclosure and claims, the singular forms "a," "an," and "the" include plural forms unless the specification indicates otherwise.

The term "and/or" as used in a phrase such as "A and/or B" herein is intended to include "A and B," "A or B," "A," and "B."

The term "$C_n$," refers to a hydrocarbon compound comprising carbon atom(s) in its molecular structure having n total carbon atom(s), or a mixture of two or more such hydrocarbon compounds. Various degrees of unsaturated carbons can present in such hydrocarbons.

The terms "paraffin," "alkane," and "saturated hydrocarbon" are used interchangeably herein and refer to hydrocarbons having a formula of $C_nH_{2n+2}$.

The terms "linear" and "normal" are used interchangeably herein and refer to hydrocarbons without side-chain branches.

The term "cracking" refers to the conversion of a given hydrocarbon molecule into two smaller hydrocarbon molecules.

The terms "isomerization" and "hydroisomerization" refer to a skeletal rearrangement of a hydrocarbon, particularly conversion of a normal paraffin into a branched paraffin.

The term "weight hourly space velocity" ("WHSV") refers to a measure of the weight of a feed mixture flowing per unit weight of a catalyst per hour.

The term "liquid hourly space velocity" ("LHSV") refers to a measure of the volume of a feed mixture flowing per unit volume of a catalyst per hour.

The term "variable oxidation state metal" refers to a metal having two or more accessible oxidation states other than a zero-oxidation state.

The term "total surface area" refers to the total specific external and internal surface area of disperse or porous solids (microporous materials), which is obtained by measuring the amount of adsorbed $N_2$ adsorption/desorption isotherms, such as specified in ISO 9277.

Unless otherwise indicated, ambient temperature (also referred to as "room temperature") is about 25° C.

Provided herein are methods for hydroisomerization of a hydrocarbon feedstock comprising contacting the hydrocarbon feedstock with hydrogen and a catalyst to yield a hydrocarbon product having an increase in branched hydrocarbons relative to the hydrocarbon feedstock. The catalyst comprises a heteroatom-doped zeolite Beta and can further comprise a metal oxide binder. In the present methods, the heteroatom-doped Beta zeolite comprises a trivalent cation as a framework metal oxide, an extra-framework species comprised of cerium and/or cobalt, and from 0.01 to 1.5 wt. % of a group VIII or VIB metal, or a combination thereof. The present heteroatom-doped Beta zeolite can further comprise a molar ratio of $SiO_2$ to the framework/extra-framework oxide greater than 10. In an aspect, the present heteroatom-doped Beta zeolites comprise a molar ratio of $SiO_2$ to $Al_2O_3$ of greater than 10. In an aspect, the present heteroatom-doped Beta zeolites comprise a metal of group VIII or VIB and/or are selective for n-heptane conversion.

In the present methods of hydroisomerization, the hydrocarbon feedstock is exposed to the catalyst under effective isomerization conditions which include operating temperatures from 100° C. to 450° C., operating pressures from 0 psig to 1000 psig, a WHSV from 0.1 $hr^{-1}$ to 10 $hr^{-1}$, and hydrogen/hydrocarbon mole ratios from 0 to 100. In an aspect, the catalyst comprises 0.1 wt. % to 1.5 wt. % Pt. The hydrocarbon feedstock comprises any of the following hydrocarbons: n-pentane, n-hexane and n-heptane and combinations thereof.

As described herein, the present methods of synthesizing a heteroatom doped-Beta zeolite comprising cerium or cobalt as an extra-framework species include the step of crystallizing a reaction mixture comprising water, $SiO_2$, and a framework metal oxide. Optionally, the reaction mixture includes a structure directing agent and/or a mineralizer. The reaction mixture comprises a molar ratio of structure directing agent cation, Q, to $SiO_2$ in the reaction mixture of 0 to 4; a molar ratio of $SiO_1$ to framework metal oxide in the reaction mixture of greater than 10; a molar ratio of water to $SiO_2$ in the reaction mixture of greater than 0; a molar ratio of alkali metal M to $SiO_2$ in the reaction mixture of from 0 to 1; and a molar ratio of $SiO_2$; to Al source in the reaction mixture of greater than 10. The present methods of synthesizing the heteroatom doped-Beta zeolite include the step of calcining the heteroatom-doped Beta zeolite wherein framework heteroatoms are converted into extra-framework species at a temperature from 100° C. to 800° C., under inert, oxidative and/or steaming conditions. The Beta zeolite has a molar ratio of $SiO_2$ to a framework metal oxide of greater than 10. The Beta zeolite also has a molar ratio of $SiO_2$ to $Al_2O_3$ of greater than about 8.

To make the present heteroatom-doped zeolites, heteroatoms are introduced into a synthesis gel before the crystallization. By utilizing the present methods, heteroatoms can be present in the framework sites and as an extra-framework species. According to DR UV-vis measurement results, many of the extra-framework species found as impurities in heteroatom-containing zeolites have a distinct dispersion compared to that of the bulk. Such species, therefore, can be used as promotors in close proximity with the zeolite framework acid sites to enhance the performance for bifunctional reactions. This is different from prior art zeolite Beta and other zeolites where heteroatoms are introduced into the framework sites post synthesis. Verification of incorporations of heteroatoms in a framework T-site of a zeolite has been limited due to available characterization techniques. Although there have been reports of incorporation indirectly, for example through catalytic testing results, whether incorporation is via framework sites or the extra-framework species has been unclear to date.

For bifunctional heptane hydroisomerization, various heteroatoms are beneficial as promotors. Such promotional effect has been confirmed with heteroatoms in the framework site or at the ion-exchange site. For example, the addition of zinc, titanium, and zirconium into a framework site to improve activity and selectivity of ZSM-48 crystals is described in US Pub. App. No. 2015/0273450A1. The maximum yield to iso-hexadecane was obtained and confirmed when the material contained titanium. For the framework incorporation as described, the activity enhancement for hydroisomerization included Mn, Fe and Ga. Introduction of different heteroatoms at the ion-exchange sites can be beneficial for activity and selectivity. Examples include La, Fe, Co etc., which can be found in the following literature: Liu et al., *Rare Earth Metals Ion-exchanged β-zeolites as Supports of Platinum Catalysts for Hydroisomerization of n-heptane*, Chin. J. Chem. Eng., 19, 278, 2011; Ushiki et al., *Co-loading of Pt and Fe on *BEA Zeolite for Enhanced Isomerization Selectivity in n-Heptane Conversion*, Chem Lett. 47, 1428-1430, 2018; and Izutsu et al., *Synthesis and Characterization of Chromium-Added Pt/Beta Zeolites and its Catalytic Performance of n-Heptane Isomerization*, Catal. Lett., 143, 486, 2013.

As described in the examples herein, the present catalysts are selective and highly active for light linear paraffins when compared to conventional monometallic Pt/Al-Beta catalyst. The present catalysts are selective for $C_5$, $C_6$ and $C_7$ mixed hydrocarbon feeds in hydroisomerization reactions. When compared to the Pt/Fe/WZrOx and Pt/Al-MOR catalyst, mixed metal oxide catalysts, the present catalyst provides the equal or greater conversion and selectivity while operating at higher temperatures.

As further taught by the examples, unconventional heteroatoms such as cerium ("Ce") and cobalt ("Co") are added to a Beta zeolite synthesis to obtain an Al-Beta zeolite, a heteroatom-doped zeolite. When applied in hydroisomerization reactions, these zeolites have conversion selectivity tradeoff patterns comparable to the conventional monometallic Pt/Al-Beta zeolites. Certain elements like tin ("Sn") did not lead to this enhancement, showing the importance of element choice. Pt/Ce, Al-Beta is selective for $C_5$, $C_6$, and $C_7$ in a mixed hydrocarbon feed hydroisomerization reaction of Pt/Fe/WZrOx, despite operating at a higher temperatures (Pt/Ce,Al-beta 250° C., Pt/Fe/WZrOx 170° C.). Advancement in the conversion-selectivity tradeoff has been confirmed and compared to conventional Pt/Al-Beta which was prepared in a similar manner.

As noted above, heteroatoms are introduced into a synthesis before crystallization of the zeolite and can be partially removed from the framework sites during calcination. This methodology is contrary to a heteroatom-containing zeolite having heteroatoms in the framework sites. According to DR UV-vis measurements, an extra-framework specie can be found as an impurity in the heteroatom-doped zeolites as a distinct dispersion compared to that of the bulk oxide and heteroatom-containing zeolites. Such extra-framework species are useful as promotors located in close proximity with the zeolite framework acid sites for enhancing performance for bifunctional reactions and properties of the catalysts used therein.

The Beta Zeolite

As described in U.S. Pat. No. 3,308,069 and U.S. Reissue Pat. No. 28,341, Beta zeolite (referred to also sometimes as "zeolite Beta") are crystalline aluminosilicate zeolites having an open three-dimensional framework of $SiO_4$ and $AlO_4$ tetrahedra cross-linked by shared oxygen atoms, so that the ratio of oxygen atoms to the total of the aluminum and silicon atoms is equal to two. The negative electrovalence of the tetrahedra containing aluminum is balanced by the inclusion within the crystal of cations, such as alkali or alkaline earth metal ions.

Zeolites possess a crystal structure, having channels of molecular dimensions. The interstitial spaces are originally occupied by water of hydration. After at least partial dehydration, these zeolites are efficient adsorbents whereby adsorbate molecules are retained within the interstitial spaces. The interstitial dimensions of openings in the crystal lattice limit the size and shape of the molecules that are adsorbed. A separation of a mixture of various molecules, based upon molecular dimensions, wherein certain molecules are adsorbed by the zeolite while others are excluded from admission is therefore possible.

According to the embodiment of the invention, Beta zeolite can have a composition that has been calculated to be:

$$[XNa(1.0\pm 0.1-X)TEA]AlO_2.YSiO_2.WH_2O$$

where X is less than 1, or less than 0.75; TEA represents tetraethylammonium ion; Y is greater than 5 but less than 100 and W is up to about 4 depending on the condition of dehydration and on the metal cation present. The TEA component is calculated by difference from the analyzed value of sodium and the ultimate theoretical cation of Al ratio of 1.0/1.

Beta zeolite is prepared from reaction mixtures containing tetraethylammonium hydroxide by heating in aqueous solution a mixture of the oxides, or materials whose chemical compositions can be represented as mixtures of the oxides such as $Na_2O$, $Al_2O_3$, $[(C_2H_5)_4N]_2O$, $SiO_2$ and $H_2O$, at a temperature of about 75° C. to 200° C. until crystallization occurs. The composition of the reaction mixture, expressed in terms of mol ratios falls within the following ranges: $SiO_2/AlO_2$ from about 10 to about 200; $Na_2O$/tetraethylammonium hydroxide (TEAOH) from about 0.0 to 0.1; $TEAOH/SiO_2$ from about 0.1 to about 1.0; and $H_2O/TEAOH$ from about 20 to about 75. The product which crystallizes from the hot reaction mixture is separated, by centrifuging or filtration, washed with water and dried. The material so obtained may be calcined by heating in air or an inert atmosphere at a temperature in the approximate range of about 400° F. to about 1700° F. or higher so long as the temperature is not sufficient to destroy the crystallinity.

To make a Beta zeolite, the method comprises reacting in aqueous media, amorphous silica solids or sols and a soluble aluminate along with aqueous solutions of tetraethylammonium hydroxide. The aluminate may be sodium aluminate or tetraethylammonium aluminate. Amorphous silica-alumina solids may be used as the source of the silica and alumina. The reaction mixture is initially continuously or periodically stirred to insure homogeneity. After this mixing, agitation may be stopped as it is unnecessary to agitate the reaction mass during the formation and crystallization of the zeolite, although mixing during such latter stages has not been found to be detrimental.

The crystallization procedures can be carried out at temperatures within the range from about 75° C. to about 200° C. The pressure during crystallization is atmospheric or at least that which corresponds to the vapor pressure of water in equilibrium with the mixture of reactants. Heating is continued until desired crystalline zeolite product is formed.

The zeolite crystals are then separated from the mother liquor and washed, with distilled water and the like.

Beta zeolite is different from other crystalline aluminosilicates in several ways. First, it has a novel structure as defined by X-ray crystallography. Second, Beta zeolite has a novel combination of adsorption properties. The adsorptive capacities for cyclohexane, n-hexane and $H_2O$ are approximately equal, or of the same order of magnitude. Also, $H_2O$ adsorption capacity does not exceed the cyclohexane adsorption. Further, the $SiO_2/AlO_2$ ratio can be high and variable and from 10 to 100 and as high as 150.

Beta zeolite catalysts can be prepared by calcining the original sodium form of Beta zeolite and/or by replacing the major portion of the sodium in the zeolite with other metallic and/or ammoniacal ions. If the calcination is carried out prior to ion exchange, some or all of the resulting hydrogen ions can be replaced by metal ions in the ion exchange process.

Beta zeolite is also useful an adsorbent in various forms. For example, a column of powder crystalline material may afford excellent results as may a pelleted form obtained by pressing into pellets a mixture of Beta zeolite and a suitable bonding agent, such as clay.

Highly active conversion catalysts can be obtained by treating the present Beta zeolites with a fluid medium containing a hydrogen ion or ion capable of conversion to a hydrogen ion in an amount sufficient to impart catalytic properties thereto. The catalysts so obtained possess a wide spectrum in magnitude of catalytic activity; can be used in extremely small concentrations; and permit certain hydrocarbon conversion processes to be carried out under practicable and controllable rates at temperatures much lower than those previously employed.

High activity catalysts contemplated are obtained by contacting the present Beta zeolites with a fluid medium containing hydrogen ions or ions capable of conversion thereto, washing the treated material free of soluble anions, and thereafter drying and thermally activating the product by heating at temperatures ranging from about 400° F. to 1700° F. or higher for a period between about one and forty-eight hours. The resulting product is an activated aluminosilicate, strongly acidic in character, which contains less than about 10 percent by weight metal and substantially corresponds to the hydrogen form of the Beta zeolite precursor material. When subsequently used alone or combined in a state of particle size of less than about 40 microns, dispersed or otherwise intimately admixed resulting product has been found to be active as a catalyst for hydrocarbon conversion.

The compositions resulting from treatment of Beta zeolite with fluid media containing hydrogen ions, ammonium ions or complex ammonium ions and metal ions, or mixtures thereof may be employed as catalysts in a wide variety of hydrocarbon conversion processes including isomerization/hydroisomerization, disproportionation, hydration of olefins, amination of olefins, oxidation, dehydrogenation, dehydration of alcohols, desulfurization, hydrogenation, reforming, hydrocracking, polymerization and the like. These catalysts are stable at temperatures ranging from ambient temperatures 70° F. up to 1000° F., including such processes in which the catalyst is periodically regenerated by burning off combustible deposits. Because of their high catalytic activities, the catalysts are useful for effecting various hydrocarbon conversion processes such as alkylation, for example, at relatively low temperatures with small amounts of catalyst, thus providing a minimum of undesirable side reactions and operating costs.

The catalysts comprising the present heteroatom-doped Beta zeolites may be used as such or as intermediates in the preparation of further modified contact masses comprising low activity or catalytically active materials which serve as a support or matrix for the aluminosilicate. The catalyst may be used in powdered, granular or molded state formed into spheres or pellets of finely divided particles having a particle size of 2 to 500 mesh. In cases where the catalyst is molded, such as by extrusion, the aluminosilicate may be extruded before drying, or dried or partially dried and then extruded. The catalyst product is then preferably pre-calcined in an inert atmosphere or may undergo calcination initially during use in the conversion process. Generally, the composition is dried between 150° F. and 600° F. and thereafter calcined in air or steam or an inert atmosphere of nitrogen, hydrogen, helium, flue gas or other inert gas at temperatures ranging from 400° F. to 1700° F. for periods of time ranging from one to forty-eight hours or more. This heating step is known as thermal activation of the catalyst.

The present catalysts can be prepared in any desired physical form including small fragments of a size best suited for operation under the specific conditions existing. Thus, the catalyst may be in the form of finely divided powder or may be in the form of pellets of 1/16" to 1/8" size, for example, obtained upon pelleting, casting, or extruding in accordance with well-known techniques.

The present catalysts are useful in a hydroisomerization process that includes catalyst having a low ratio of silica to alumina. For example, the ratio of silica to alumina in the zeolite can be less than about 200:1, such as less than about 110:1, or less than about 100:1, or less than about 90:1, or less than about 75:1. In various aspects, the ratio of silica to alumina can be from 50:1 to 200:1, such as 20:1 to 160:1, or 30:1 to 100:1.

In an aspect, the present catalysts include a metal hydrogenation component. The metal hydrogenation component is typically a Group VIB and/or a Group VIII metal. In an aspect, the metal hydrogenation component can be Pt, Pd, or a mixture thereof. In an alternative, the metal hydrogenation component can be a combination of a non-noble Group VIII metal with a Group VIB metal.

The metal hydrogenation component is added to the catalyst in any convenient manner. One technique for adding the metal hydrogenation component is by incipient wetness. For example, after combining a zeolite and a binder, the combined zeolite and binder can be extruded into catalyst particles. These catalyst particles are then exposed to a solution containing a suitable metal precursor. Alternatively, metal can be added to the catalyst by ion exchange, where a metal precursor is added to a mixture of zeolite (or zeolite and binder) prior to extrusion.

The amount of metal in the catalyst can be at least 0.1 wt. % based on catalyst, or at least about 0.15 wt. %, or at least about 0.2 wt. %, or at least about 0.25 wt. %, or at least about 0.3 wt. %, or at least about 0.5 wt. % based on catalyst. The amount of metal in the catalyst can be about 20 wt. % or less based on catalyst, or about 10 wt. % or less, or about 5 wt. % or less, or about 2.5 wt. % or less, or about 1 wt. % or less. Where the metal is Pt, Pd, another Group VIII noble metal, or a combination thereof, the amount of metal can be from about 0.1 to about 5 wt. %, from about 0.1 to about 2 wt. %, or about 0.25 to about 1.8 wt. %, or about 0.4 to about 1.5 wt. %. For aspects where the metal is a combination of a non-noble Group VIII metal with a Group VIB metal, the combined amount of metal can be from 0.5 wt. % to 20 wt. %, or 1 wt. % to 15 wt. %, or 2.5 wt. % to 10 wt. %.

The present catalysts can also include a binder. In some embodiments, the dewaxing catalysts can be formulated using a low surface area binder, where a low surface area binder represents a binder with a surface area of 100 $m^2/g$ or less, or 80 $m^2/g$ or less, or 70 $m^2/g$ or less. The amount of zeolite in a catalyst formulated using a binder can be from about 30 wt. % zeolite to 90 wt. % zeolite relative to the combined weight of binder and zeolite. The amount of zeolite is at least about 50 wt. % of the combined weight of zeolite and binder, such as at least about 60 wt. % or from about 65 wt. % to about 80 wt. %.

In accordance with various embodiments of the invention, a zeolite can be combined with binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture. The amount of framework alumina in the catalyst can range from 0.1 to 3.33 wt. %, or 0.1 to 2.7 wt. %, or 0.2 to 2 wt. %, or 0.3 to 1 wt. %.

Hydroisomerization Processes

Hydroisomerization of linear and mono-branched paraffins (alkanes) can improve octane rating in gasoline fuel products. Paraffin isomerization using a bifunctional catalyst, such as a zeolite or mixed metal oxide catalyst, promotes paraffin isomerization through dehydrogenation, protonation forming a carbenium ion, and skeletal rearrangement of the carbenium ion through mechanisms such as those involving a cyclopropyl cation.

In conventional paraffin hydroisomerization processes, a hydrocarbon feed is heated in the presence of hydrogen and a suitable bifunctional catalyst. For example, U.S. Patent Application Publication 2013/0324782 describes one of the conventional paraffin isomerization processes where a bifunctional catalyst is used. In addition, U.S. Pat. Nos. 6,080,904 and 6,124,232 provide details of bifunctional catalysts which are acidic metal oxide catalysts, and paraffin isomerization processes where $C_5$ and $C_6$ linear (normal) paraffins undergo isomerization using such catalysts. Other catalysts including chloride alumina, sulfated zirconia, and certain zeolites can isomerize $C_5$ & $C_6$ linear paraffins with high selectivity against cracking.

By contrast, $C_{7+}$ normal paraffins are prone to cracking under isomerization reaction conditions, particularly at higher reaction temperatures. Excessive cracking leads to yield loss of the desired branched paraffins and lower octane numbers. Without being bound by any theory or mechanism, cracking is believed to occur through β-scission of the cation intermediate. During β-scission, $C_5$ and $C_6$ normal paraffins lead to formation of an ethyl cation, a primary carbenium ion that forms with difficulty. In contrast, $C_{7+}$ paraffins may form more stable and more easily generated secondary or tertiary carbenium ions upon β-scission. As such, it can sometimes be difficult to mitigate cracking of $C_{7+}$ paraffins under isomerization reaction conditions, given the favorable thermodynamics for promoting cracking.

U.S. shale oil production is rapidly increasing in volume. Shale oils typically require additional processing for use in fuel blends. While branched hydrocarbons with higher octane ratings are desirable as blending components for the manufacture of premium gasolines, $C_7$ and $C_8$ linear paraffins are predominant components of this hydrocarbon resource and tend to crack under conventional processing. Although catalytic reforming is viable for the $C_{8+}$ components of shale oil naphtha, catalytic reforming is energy inefficient and results in a significant fraction of the hydrocarbon resource unconverted.

As discussed above, hydroisomerization of normal paraffins operates to increase octane number, but excessive cracking of $C_{7+}$ normal paraffins is problematic in various respects. To combat the thermodynamic favorability of cracking $C_{7+}$ normal paraffins, isomerization is conducted at lower temperatures and lower feed mixture conversions, which can be undesirable from a processing efficiency standpoint. As such, it may be difficult to upgrade the octane number of hydrocarbon resources having a significant fraction of normal paraffins, such as naphtha, particularly those with a high fraction of $C_{7+}$ unbranched and monobranched paraffins.

As provided herein, the hydroisomerization process includes using catalysts that can selectively convert high carbon number light paraffin in a mixed feed to achieve maximum conversion levels of $C_7$ determined by equilibrium, followed by a separation unit to remove the partially converted $C_5$ and $C_6$, and conducting further hydroisomerization on the unconverted light paraffins to obtain highly branched products. In the present methods, a hydrocarbon feedstock for hydroisomerization processing can comprise $C_5$-$C_{30}$ normal paraffins, such as $C_5$-$C_7$ normal paraffins, or $C_{7+}$ normal paraffins and/or monobranched paraffins. The hydrocarbon feedstock further comprises $C_{7+}$ normal paraffins, such as $C_5$-$C_{30}$ normal paraffins, as well as monobranched paraffins (e.g., a $C_5$ monobranched paraffin, a $C_6$ monobranched paraffin or a $C_{7+}$ monobranched paraffin), a $C_5$ normal paraffin, a $C_6$ normal paraffin, or any combination thereof. Thus, the hydrocarbon feedstock comprises normal or monobranched $C_5$ paraffins, normal or monobranched $C_6$ paraffins, and normal or monobranched $C_7$ paraffins. Optionally, at least some normal or monobranched $C_8$ paraffins are be present in such hydrocarbon feedstocks as well. Other hydrocarbon feedstocks useful with the present catalysts can comprise $C_{10}$-$C_{10}$ normal paraffins or monobranched paraffins. Any of the foregoing hydrocarbon feedstock might further comprise one or more aromatic compounds as well.

Optionally, one or more naphthenic compounds are combined with the hydrocarbon feedstock. By including one or more naphthenic compounds as a co-feed, the incidence of cracking may be lowered still further. About 10 wt. % or more naphthenic compounds can be present in combination with the hydrocarbon feedstock. Suitable naphthenic compounds include branched naphthenic compounds such as methylcyclopentane (MCP), methylcyclohexane (MCH), or any combination thereof. Other suitable branched naphthenic compounds such as ethylcylopentane, propylcyclopentane, 1,1-dimethylcyclopentane, 1,1-dimethylcyclohexane, ethylcyclohexane, propylcyclohexane, and the like are also be suitable for use in the processes described herein including bicyclic naphthenic compounds as well. In general, any naphthenic compound that may form a tertiary carbenium ion under isomerization reaction conditions can be used effectively with the present catalysts in hydroisomerization processes.

In the hydroisomerization process, one or more catalysts are contacted with the hydrocarbon feedstock under one or more of the following isomerization reaction conditions: temperatures ranging from about 150° C. to about 300° C., or from about 170° C. to about 270° C.; a mole ratio of hydrogen to hydrocarbon feedstock ranging from about 1:1 to about 3:1; pressures ranging from about 100 psig to about 350 psig; and a liquid hourly space velocity ranging from about 0.5 $h^{-1}$ to about 6 $h^{-1}$. Hydrogen partial pressures range from about 50 kPa to about 2000 kPa, for example. In particular examples, the hydroisomerization reaction conditions include a liquid hour space velocity of about 6 $hr^{-1}$ or less, or about 5 $hr^{-1}$ or less, or about 4 $hr^{-1}$ or less, and from about 2 $hr^{-1}$ to about 5 $hr^{-1}$. The hydroisomerization reaction conditions are such that the hydroisomerization reaction is carried out in the gas phase, a supercritical phase, or a liquid phase. The hydroisomerization reaction conditions provide about 95% or less conversion, or about 90% or less conversion, or about 85% or less conversion, or about 80% or less conversion, or about 75% or less conversion, or about 70% or less conversion of the $C_5$-$C_7$ normal paraffins. Utilizing the present catalysts, about 70% to about 90% conversion of $C_{7+}$ normal paraffins can be provided. Cracking yields for n-heptane are about 10 wt. % or less, and the ratio of n-heptane isomerization: cracking yield is about 10 or more, such as about 10 to about 25, or about 10 to about 20.

Pt/Fe/WZrOx Catalysts

As taught in co-pending application, 2021EM062-US, a mixed metal oxide catalyst referred to as a Pt/Fe/WZrOx catalyst (or EMM-62), is at least partially crystalline and comprises tungsten, zirconium, and a variable oxidation state metal. The variable oxidation state metal comprises a metal selected from the group consisting of Fe, Mn, Co, Cu, Ce, Ni, and any combination thereof. The Pt/Fe/WZrOx catalyst has between about 5 wt. % and about 25 wt. % tungsten, between about 40 wt. % and about 70 wt. % zirconium, and between about 0.01 wt. % and about 5 wt. % variable oxidation state metal, each based on a total mass of the mixed metal oxide. The Pt/Fe/WZrOx catalyst has a total surface area of about 50 $m^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically.

To make the Pt/Fe/WZrOx catalyst, zirconium, tungsten, and a variable oxidation state metal are combined in a reaction mixture under alkaline conditions having a pH of about 7.5 or greater. The variable oxidation state metal comprises a metal selected from the group consisting of Fe, Mn, Co, Cu, Ce, Ni, and any combination thereof. Under the alkaline conditions, a slurry comprising a co-precipitate reaction product formed from the zirconium, the tungsten, and the variable oxidation state metal is obtained. The slurry is digested to form an amorphous digestion product from the co-precipitate reaction product. The amorphous digestion product is calcinated in air at a temperature ranging from about 700° C. to about 900° C. to obtain a mixed metal oxide that is at least partially crystalline and comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide. This mixed metal oxide has a total surface area of about 50 $m^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically.

Pt/Al-MOR Catalysts

As described in published international patent applications, WO2016/126431 and WO 2018/160327, the Pt/Al-MOR catalysts have a mesopore surface area of greater than 30 mu/g and comprising agglomerates composed of primary crystallites, wherein the primary crystallites have an average primary crystal size as measured by TEM of less than 80 nm, an aspect ratio of less than 2 and a total surface area of greater than 500 m$^2$/g. In some embodiments, Pt/Al-MOR catalysts (also referred to sometimes as EMM-34) has a ratio of the mesopore surface area to the total surface area of greater than 0.05, and is synthesized from TEA or MTEA.

The Pt/Al-MOR catalyst, also referred to as meso-mordenite, is a zeolite synthesized from structure directing agents TEA (tetraethyl ammonium cation) or MTEA (methyl triethyl ammonium cation) and having a mesopore surface area of greater than 30 m$^2$/g and comprising agglomerates composed of primary crystallites, wherein the primary crystallites have an average primary crystal size as measured by TEM of less than 80 nm and an aspect ratio of less than 2.

The Pt/Al-MOR catalyst has a mesopore surface area, as measured by BET of greater than 30 m/g, greater than 40 r/g, and in some cases greater than 45 m$^2$/g. Pt/Al-MOR catalysts comprise agglomerates, typically irregular agglomerates, which are composed of primary crystallites which have an average primary crystal size as measured by TIM of less than 80 nm, less than 70 nm and less than 60 nm, for example, less than 50 nm. The primary crystallites may have an average primary crystal size in the range of greater than 20 nm, optionally greater than 30 nm to less than 80 nm as measured by TEM.

Optionally, the primary crystals of Pt/Al-MOR catalysts have an average primary crystal size of less than 80 nm, less than 70 nm, and in some cases less than 60 nm, in each of the a, b and c crystal vectors as measured by X-ray diffraction. The primary crystallites may optionally have an average primary crystal size in the range of greater than 20 nm, optionally greater than 30 nm to less than 80 nm, in each of the a, b and c crystal vectors, as measured by X-ray diffraction.

Pt/Al-MOR catalyst will generally comprise a mixture of agglomerates of the primary crystals together with some unagglomerated primary crystals. The majority of Pt/Al-MOR catalyst, for example, greater than 80 wt. % or greater than 90 wt. %, will be present as agglomerates of primary crystals. The agglomerates are typically of irregular form. For more information on agglomerates. See e.g., Walter, D., Primary Particles—Agglomerates—Aggregates, in Nanomaterials, Deutsche Forschungsgerneinschaft (DFG), Wiley, 1-24, 2013.

Optionally, Pt/Al-MOR catalysts comprise at least 50% by weight, at least 70% by weight, advantageously at least 80% by weight, and at least 90% by weight and optionally substantially consists of the irregular agglomerates composed of primary crystallites having a primary crystal size of less than 80 run, less than 70 nm, and less than 60 nm, for example, less than 50 nm. Pt/Al-MOR catalyst comprises less than 10% by weight of primary crystallites having a size of more than 80 nm as assessed by TEM. Pt/Al-MOR catalyst has irregular agglomerates composed of crystallites having a crystal size as measured by TEM of less than 80 nm. Pt/Al-MOR catalyst is substantially free, for example, contains less than 10% by number as assessed by TEM, of needle or platelet crystals.

The primary crystallites of Pt/Al-MOR catalyst have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

The agglomerates of the primary crystallites are typically of irregular form and may be referred to as being "secondary" particles because they are formed of agglomerates of the crystallites, which are the "primary" particles. The primary crystallites may have a narrow particle size distribution such that at least 90% of the primary crystallites by number have an average primary crystal size in the range of from 20 to 80 nm and/or from 20 to 60 nm, as measured by TEM.

The Pt/Al-MOR catalyst has a total surface area of greater than 500 m$^2$/g, greater than 550 m$^2$/g, and in some cases greater than 600 m$^2$/g. The total surface area includes the surface area of the internal pores (zeolite surface area) and also the surface area on the outside of the crystals (the external surface area) The total surface area is measured by BET. The ratio of mesopore surface area to the total surface area for Pt/Al-MOR is greater than 0.05. The Pt/Al-MOR catalyst has a mesopore volume of greater than 0.1 mL/g, and/or greater than 0.12 mL/g, and in some cases greater than 0.15 mL/g.

EXAMPLES

The features of the present methods and compositions are described in the following non-limiting examples.

Example 1

Synthesis of Heteroatom-Doped Beta Zeolite

Zeolite Synthesis

Aluminum nitrate ($Al(NO_3)_3 9H_2O$) and a heteroatom nitrate salt (such as $Ce(NO_3)_3 6H_2O$) were dissolved in deionized water to form a transparent solution. The transparent solution was added to a monodispersed colloidal silica (40 wt. % suspension in $H_2O$). Tetraethylammonium hydroxide ("TEAOH") solution, 35 wt. %) was added and mixed to obtain a homogeneous gel. The homogeneous gel was placed inside a Teflon-lined steel autoclave, and heated under hydrothermal conditions at 150° C. for about 5 to about 6 days under 20 rpm rotation. The molar ratio was as follows: $SiO_2$:TEAOH:$Al(NO_3)_3$:$M(NO_3)$x:$H_2O$ equal to 1:0.4:0.05:y:16 where typically y is 0.005 or 0.01, or y is 0 for obtaining the Al-Beta zeolite used as the control catalyst.

Zeolite was collected by centrifuge (typically 12000 rpm for 5 minutes, three repetitions), and was dried in 120° C. oven for overnight. Calcination was conducted at 550° C. for six (6) hours, with a three-hour ramping period. Finally, ion-exchange with Pt $(NH_3)_4(NO_3)_2$ was conducted for 24 hours in 10 grams solution/1 gram zeolite ratio to obtain 0.6 wt. % Pt in the final product. Zeolite was collected by centrifuge and was calcined at 550° C. for three (3) hours.

Characterization

Figure 2:
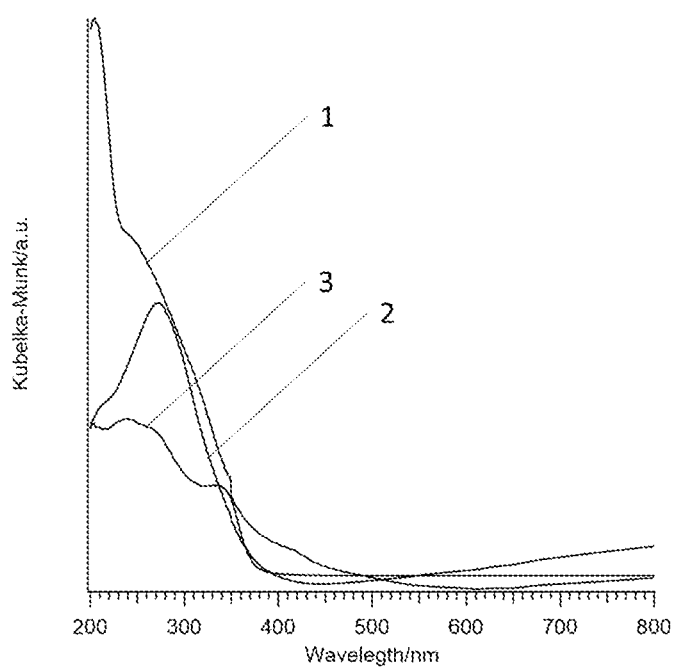
FIG. 2 is a graph of DR UV-vis results for Ce-doped Al-Beta zeolites before and after calcination in reference to $CeO_2$ (signal reduced to 1/20 for visual clarity).

X-ray diffraction pattern ("XRD") of the Ce-doped Al-Beta zeolite (also referred to herein as "Ce,Al-Beta") with Si/Ce=100 is shown in FIG. 1, top line, and compared to Al-Beta zeolite (also referred to herein as "Al-Beta") FIG. 1, bottom line. Highly crystalline *BEA type zeolite frameworks (also referred to herein as BEA, or Beta zeolite, or Beta structure type zeolite) were obtained in the presence of cerium ("Ce") in a synthetic gel under these crystallization conditions. DR UV-vis results for the Ce-doped zeolite before and after calcination are shown in FIG. 2. Ce,Al-Beta before calcination is shown in line 1. Ce,Al-Beta after calcination is shown in line 2. The absorption intensity in terms of Kubelka-Munk function of reference $CeO_2$ was reduced to 1/20 of the original values for simplicity in the comparison. FIG. 2, line 3.

DR UV-vis spectra detect the state of the heteroatom through ligand to metal charge transfer band or "LMCT" band. In the case the heteroatom is in a mono-atomic state, this corresponds to the charge transfer from oxygen to the metal. When forming oligomers or a bulk oxide, this charge transfer corresponds to the electron transfer from the HOMO to the LUMO electron band. Thus, the absorption peak, corresponding to the energy of absorbed phonon indicates the degree of isolation (or the oligomerization) of the heteroatom oxide. In many cases, this is a measure of qualitatively investigating the state of the heteroatom. As shown, the state of Ce changes before and after the calcination step, and the degree of isolation decreases through this treatment. This result shows that in the calcined zeolite, oligomeric cerium oxide is formed at the extra framework sites. In comparison to the reference spectra of bulk $CeO_2$, the absorption edge is shifted to shorter wavelength, showing that the degree of oligomerization does not form a bulk structure.

These characterization results show that product obtained is a composite of Beta zeolite and nanoclusters of CeOx species, most likely in close proximity with the framework due to the retention of high dispersion.

Example 2

$C_7$ Hydroisomerization Reaction Using Sized Zeolite Powders

Calcined zeolite powders were sized through No. 40/60 sieves. A reaction was conducted using high-throughput fixed bed reactor using the following activation procedure:

Temperature was increased to 250° C. (60° C./hour ramp rate) under $N_2$ flow (100 standard cubic centimeters per minute ("sccm")) and was kept at 250° C. for an hour. Then, the temperature was reduced to 220° C. (60° C./hour ramp rate), and the reactor flow was changed to $H_2$ with a back pressure of 200 pounds per square inch gauge ("psig"). The catalyst was reduced with $H_2$ for 3 hrs. (100 sccm). After that, the reactor temperature was set to the designated temperature for reaction runs. Hydrocarbon feed flow had an $H_2$:n-$C_7$ molar ratio set to 2:1 with partial pressures of $H_2$ and $C_7$ being 137.1 pounds per square inch absolute ("psia") and 70.4 psia, respectively.

Figure 3:
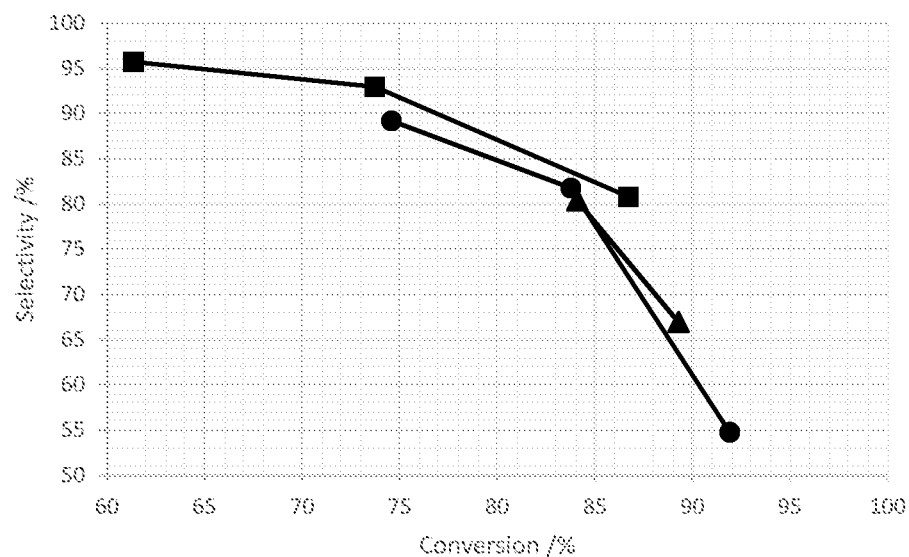
FIG. 3 shows isomerization selectivity (%) versus conversion of n-Heptane (%) of heteroatom-doped zeolites at 230° C. where WHSV equal to 2, 4, 6 per hour.

As shown in FIG. 3, Ce-doped zeolites exhibited better-quality conversion-selectivity tradeoff curves towards isomerized products compared to that of non-doped counterpart. The square symbol of FIG. 3 depicts the conversion by Pt/Ce,Al-Beta (WHSV=2, 4, 6 h$^{-1}$). Similarly, the triangle represents Pt/Al-Beta, the circle, Pt/Co,Al-Beta, each at WHSV=2, 4, 6 h$^{-1}$ at 250° C. For example, at conversion levels approximately 74%, +5% increment in the selectivity is confirmed. Note that the conversion-selectivity tradeoff of platinum-doped Al-Beta zeolite (or "Pt/Al-Beta") far outperforms the results seen in the previous literatures (ex. Wang 1997).

Figure 4:
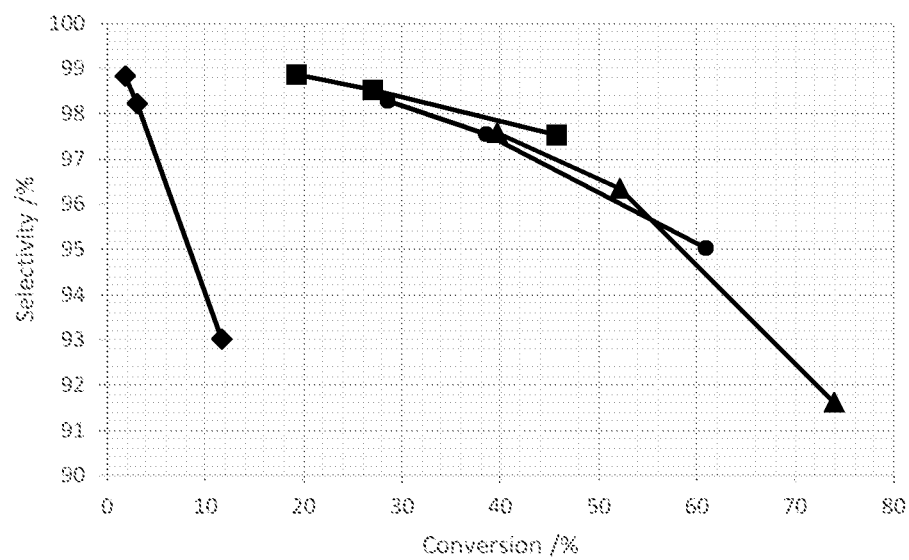
FIG. 4 shows isomerization selectivity (%) versus conversion of n-Heptane (%) of heteroatom-doped zeolites at 250° C., WHSV equal to 2, 4, 6 per hour or 4, 6 per hour.

Interestingly, framework incorporation of Sn led to loss in selectivity to isomerized product, leaving cracking as the prominent reaction pathway. FIG. 4. Previously, the introduction of zirconium ("Zr") was shown to lead to a significant increment in the reaction temperature to achieve comparable conversion levels. See e.g., US Pub. No. 2015/0273450. Here, the maximum yield was also reduced, making this material inferior compared to the other counterparts. As such, correct choice of the dopant element is important for improving the performance. As shown in FIG. 4, the square represents results using Pt/Ce,Al-Beta, the circle, Pt/Co,Al-Beta, and the diamond, Pt/Sn,Al-Beta, each at WHSV=2, 4, 6 h$^{-1}$ at 250° C.; the triangle representing results using Pt/Al-Beta at WHSV=4, 6 h$^{-1}$ at 230° C.

FIG. 3 shows isomerization selectivity (%) versus conversion of n-Heptane (%) for heteroatom-doped zeolites: (1) Pt/Al-Beta having Pt at 0.6 wt. % and Si/Al is 20; (2) Pt/Ce,Al-Beta having Pt at 0.6 wt. %, Si/Al is 20 and Si/Ce equal to 100; and (3) Pt/Co,Al-Beta having Pt at 0.6 wt. % and Si/Al is 20, and Si/Co equal to 200, each at 250° C. where WHSV equal to 2, 4, 6. FIG. 4 shows isomerization selectivity (%) versus conversion of n-Heptane (%) for heteroatom-doped zeolites: (1) Pt/Al-Beta having Pt at 0.6 wt. % and Si/Al is 20; (2) Pt/Ce,Al-Beta having Pt at 0.6 wt. %, Si/Al is 20 and Si/Ce equal to 100; (3) Pt/Co,Al-Beta having Pt at 0.6 wt. % and Si/Al is 20, and Si/Co equal to 200; (4) Pt/Sn,Al-Beta having Pt, at 0.6 wt. % and Si/Al is 20 and Si/Sn equal to 100 (prepared using $SnCl_2.5H_2O$), each at 230° C. where WHSV equal to 2, 4, 6.

This example confirms heteroatom doped zeolites benefit as an advanced bifunctional catalyst for enhancing the conversion-selectivity tradeoff in hydroisomerization reactions.

Example 3

Hydroisomerization Run Using $C_5$, $C_6$, and $C_7$ Mixture as Light Paraffin Model Calcined zeolite powders were sized through No. 40/60 sieves. A reaction was conducted using high-throughput fixed bed reactor unit using the following activation procedure: Temperature was increased to 300° C. (60° C./hour ("hr.") ramp rate) under $N_2$ flow (100 sccm) and was kept at 300° C. for 1 hr. Temperature was reduced to 220° C. (60° C./hr. ramp rate), and the reactor flow was changed to $H_2$ with a back pressure of 350 psig. The zeolite was reduced with $H_2$ for 24 hours (100 sccm). After that, the reactor temperature was set to the designated temperature for reaction runs. The hydrocarbon feed flow was as follows: n-$C_5$: n-$C_6$: n-$C_7$=1:1:1 (by weight); $H_2$:n-paraffin molar ratio=2:1 (by molar). The total pressure of the reactor was set to 180 psia.

Figure 5A:
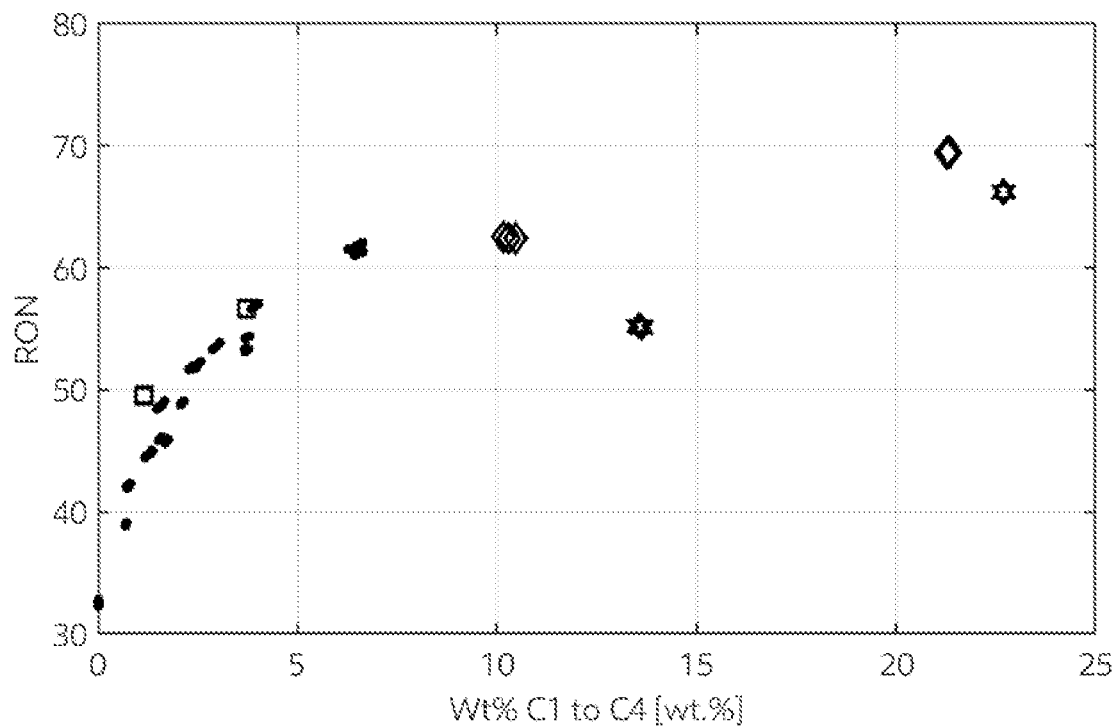
FIG. 5A shows RON increments relative to light gas ($C_1$ to $C_4$) wt. % formation at 250° C. and LHSV equal to 3, 6 per hour at 250° C. Results for the catalyst Pt/Fe/WZrOx run at 170° C.
Figure 5B:
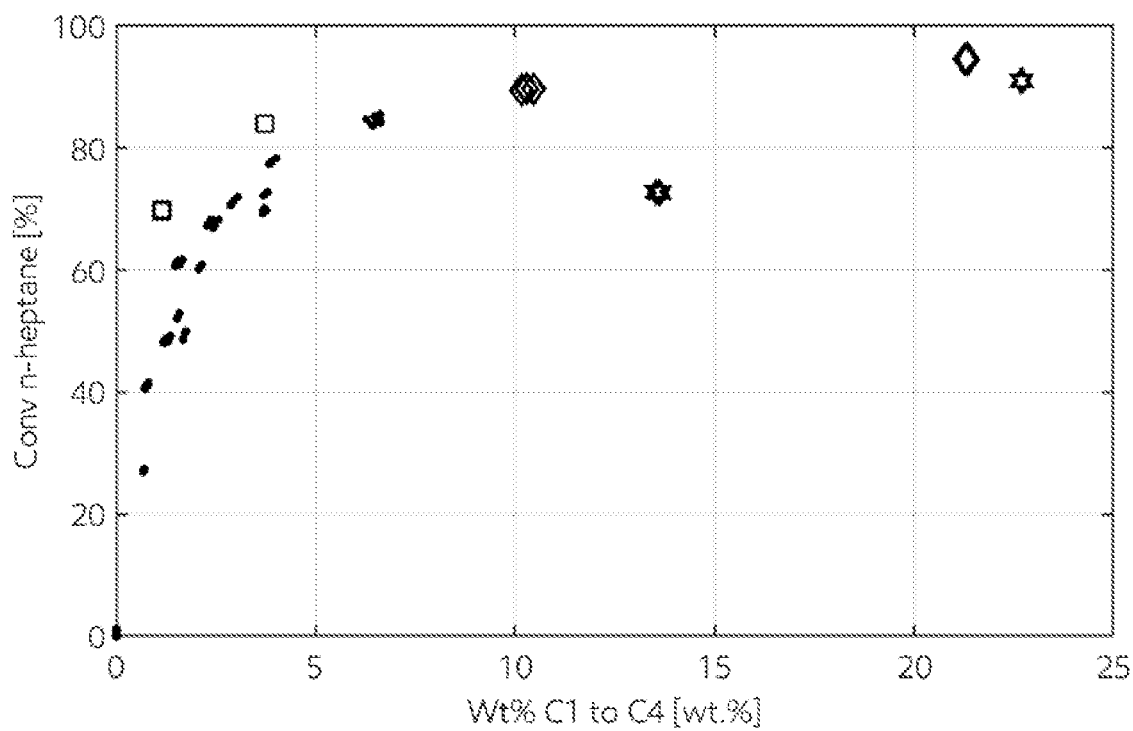
FIG. 5B is a graph showing n-$C_7$ conversion relative to the light gas formation due to cracking.

FIG. 5A shows research octane number ("RON") increments relative to light gas ($C_1$ to $C_4$) formation at 250° C. where the reaction ran at weight hour specific velocity ("WHSV") equal to 3, 6 per hour. The square in FIG. 5A represents Pt/Ce,Al-Beta, the diamond, Pt/Al-Beta, the hexagram, Pt/Al-MOR, and the circle Pt/Fe/WZrOx, each at WHSV=3, 6 h$^{-1}$. FIG. 5B shows a conversion of n-heptane (in wt. %) versus $C_1$ to $C_4$ (in wt. %). The square in FIG. 5B represents Pt/Ce,Al-Beta, the diamond, Pt/Al-Beta, the hexagram, Pt/Al-MOR, and the circle, Pt/Fe/WZrOx, each at WHSV=3, 6 h$^{-1}$.

As shown in these FIG. 5A and FIG. 5B, Ce-doped Al-Beta zeolite exhibited a step out performance for selectively isomerizing the feed to increase RON under limited cracking. For example, Pt/Ce,Al-Beta only formed approximately 1 wt. % of light gas cracked products while providing +18 boost in RON, which is comparable or slightly better than that of Pt/Fe/WZrOx, a mixed metal oxide catalyst used in this type of reaction. Note that the reaction temperatures were at 250° C. and 170° C. for Pt/Fe/WZrOx (EMM-62), and the Al-Beta zeolite samples made with the present methods were run at a more severe conditions favoring cracking. Because mixed metal oxide-based catalysts are capable of running at lower temperatures, they have a performance advantage when used for this purpose. However, the current example shows that Al-Beta zeolites having comparable performance with modified mixed metal oxide counterparts.

The contrast with pristine Pt/Al-Beta zeolite is apparent from the gradient for RON improvement per total light gas formed. The results support Ce acting as a promotor of selectivity. Pt/Al,MOR is the incumbent zeolite used for light paraffin isomerization, and was used as a model reference for comparison. This zeolite used is described in PCT publication number WO2018/160327 at ¶¶ [0053], [0055], [0058], [0059] to [0064], incorporated herein by reference. Platinum Al-MOR (Pt/Al-MOR) had a higher cracking selectivity compared to the Pt/Ce,Al-Beta zeolite, presumably due to the stronger acidity of the zeolite. These comparative results reinforce a practical advantage of Pt/Ce,Al-Beta zeolite relative to that of the other zeolite based hydroisomerization catalysts.

Also, for $C_7$ conversion levels in a feed mixture, formation of light gas was significantly suppressed with Pt/Ce, Al-Beta zeolite compared to other catalysts under same current conditions. FIG. 5B. The impact of Ce addition appears to be enhanced in the case of a mixed paraffin feed in comparison with Pt/Al-Beta zeolite. See, results with pure n-$C_7$ feed, FIG. 4, another notable advantage for enhancing the performance of the hydroisomerization process in general. Most conventional zeolite-based paraffin isomerization units can selectively convert $C_5$ and $C_6$, but have limits on converting $C_7$ due to concentration levels in the hydrocarbon feedstock. The present methods are advantageous because existing isomerization capabilities can be utilized for overall conversation without an upstream purification process, reducing the capex needed for installing a new reactor.

Figure 6:
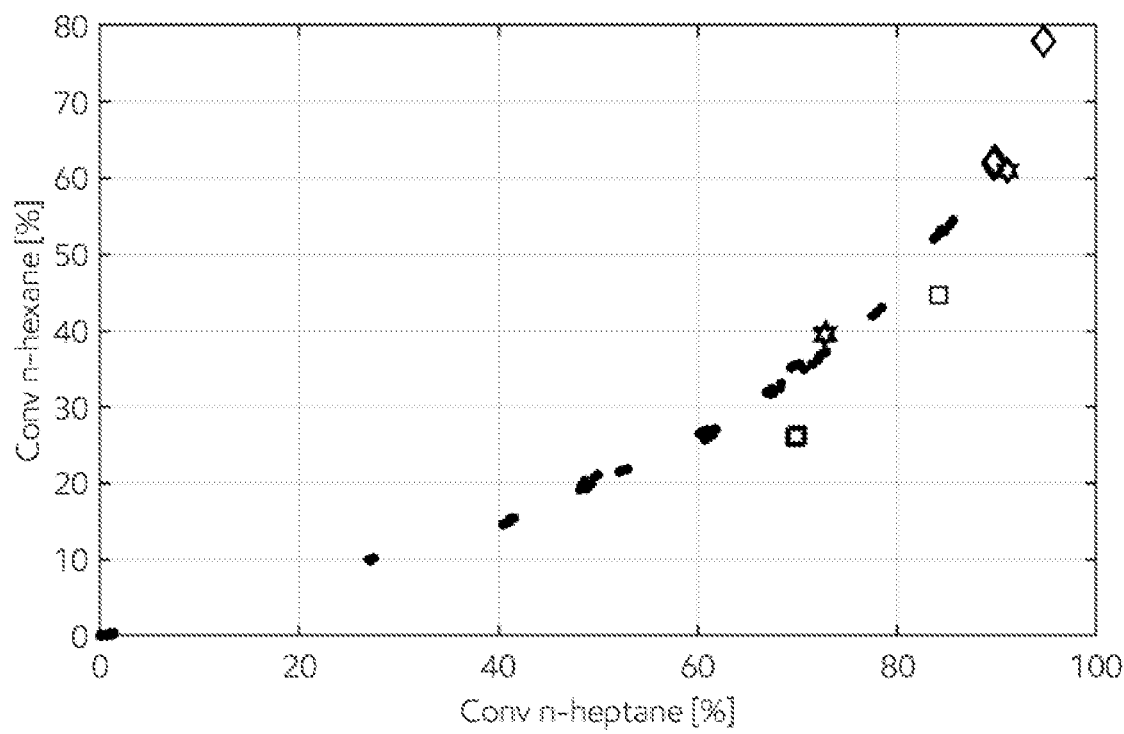
FIG. 6 shows relative conversion levels of n-$C_6$ and n-$C_7$ for four catalysts described in Example 3 at LHSV equal to 3, 6 per hour at 250° C. Results for the catalyst Pt/Fe/WZrOx run at 170° C.

As shown in FIG. 6, the square represents Pt/Ce,Al-Beta, the diamond, Pt/Al-Beta, the hexagram, Pt/Al-MOR, and the circle, Pt/Fe/WZrOx, each at LHSV=3, 6 $h^{-1}$. The relative conversion of $C_7$ versus $C_6$ for Pt/Ce,Al-Beta, Pt/Al-Beta and Pt/Fe/WZrOx are each provided. Pt/Ce,Al-Beta zeolite can be differentiated from the other catalysts as $C_7$ is converted more preferentially over $C_6$ using Pt/Ce,Al-Beta zeolite. The same trend was further shown through a comparison with $C_5$ (results not shown). This result illustrates the difference in the nature of the active site and thus the influence of the heteroatom doping onto the zeolite.

Preferential conversion of $C_7$ can be valuable in designing processes where light paraffin feeds ($C_5$-$C_7$) are first converted to achieve maximum conversion levels of $C_7$ (determined by equilibrium) and followed by a separation unit to remove the partially converted $C_5$ and $C_6$ which can be further treated using the existing light paraffin hydroisomerization unit. Most conventional paraffin isomerization units are made to selectively convert $C_5$ and $C_6$, and this limits the $C_7$ concentration levels in the hydrocarbon feedstock. However, as noted above, existing isomerization capacities can be utilized for the overall conversion, reducing the capex needed for installing a new reactor.

Example 4

$C_7$ Hydroisomerization Reaction Using Zeolite Extrudates with Alumina Binder The reaction was conducted with high-throughput fixed bed reactor using 70/30 zeolite/alumina extrudates to show that the extruded materials are also active for this reaction.

The reaction conditions were as follows: The loaded catalyst was pre-conditioned by heating the reactor from 100° C. to 400° C. with $H_2$ flow at 200 cubic centimeters per hour for 6 hours. Two 100 cubic centimeters ("cc") ISCO pumps were alternated to introduce chemical grade n-heptane feed so that there was no interruption in the flow. The feeds were pumped through heated lines to the reactor and brooks mass flow controller was used to set the hydrogen flow rate. The pressure was maintained at 350 psig. The feed was then pumped through the catalyst bed held at the reaction temperature of 230° C. at different LHSVs, hydrogen:hydrocarbon mole ratio of 2:1 and a pressure of 350 psig. The liquid products exiting the reactor flowed through heated lines and was analyzed using gas chromatograph with FID detector.

Figure 7:
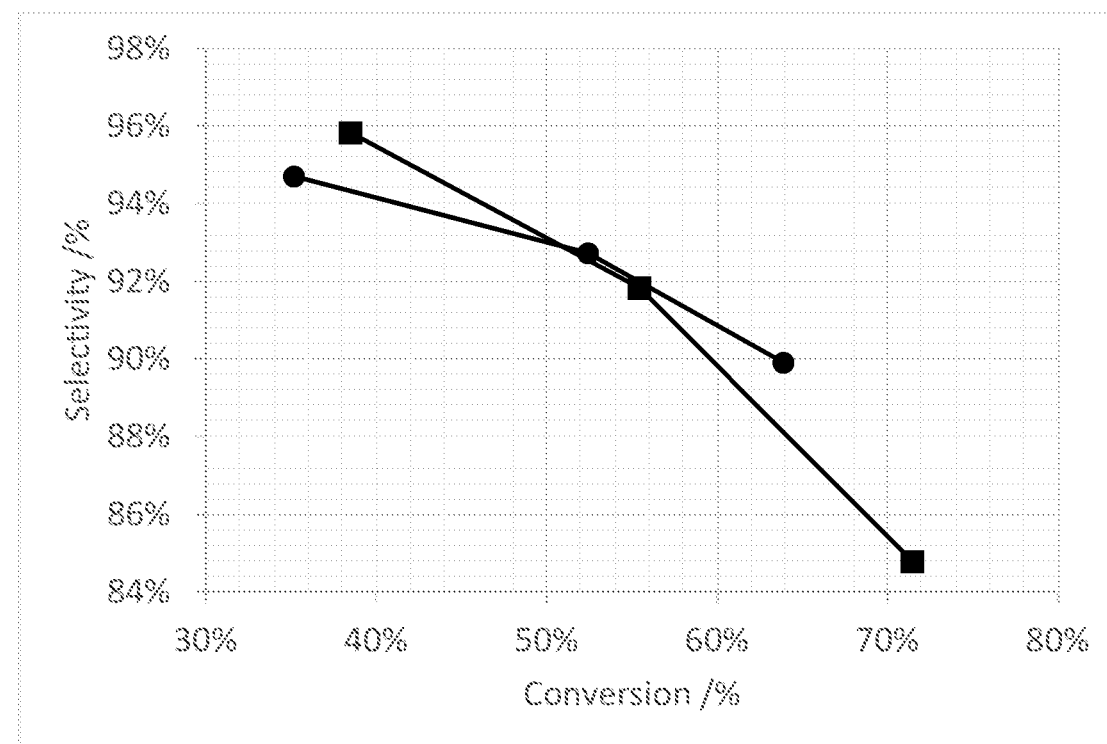
FIG. 7 shows isomer selectivity versus conversion at 230° C. at a WHSV equal to 0.75, 1, 1.5 $h^{-1}$.

In comparison to the results of Example 2, Co loading on Co,Al-Beta zeolite was increased from Si/Co=200 to Si/Co=100. These new zeolites lead to similar conversion-tradeoff curves with the Ce counterpart. FIG. 7 where the square symbol depicts conversion by Pt/Ce,Al-Beta (LHSV=0.75, 1, 1.5 $h^{-1}$) and the circle represents Pt/Co,Al-Beta (LHSV=0.75, 1, 1.5 $h^{-1}$). This result shows that the heteroatom loading also plays a key role in the catalytic performance as a promotor, and that the extruded zeolites remain active for this reaction.

Many alterations, modifications, and variations will be apparent to those skilled in the art in light of the foregoing description without departing from the spirit or scope of the present disclosure and that when numerical lower limits and numerical upper limits are listed herein, ranges from any lower limit to any upper limit are contemplated.

We claim:

1. A method for hydroisomerization of a hydrocarbon feedstock comprising contacting the hydrocarbon feedstock with hydrogen and a catalyst to yield a hydrocarbon product having an increase in branched hydrocarbons relative to the hydrocarbon feedstock, wherein the catalyst comprises a heteroatom-doped Beta zeolite having a trivalent cation as a framework metal oxide, an extra-framework species comprised of cobalt, and from 0.01 to 1.5 wt. % of a group VIII or VIB metal, or a combination thereof, the hydrocarbon feedstock comprises $C_5$-$C_{30}$ normal paraffins and/or $C_5$-$C_{30}$ monobranched paraffins and the heteroatom-doped Beta zeolite is selective for n-heptane conversion, wherein the catalyst further comprises between 5 wt. % and 25 wt. % tungsten, between 40 wt. % and 70 wt. % zirconium, and a metal oxide binder.

2. The method of claim 1, wherein the heteroatom-doped Beta zeolite further comprises a molar ratio of $SiO_2$ to the framework/extra-framework oxide greater than 10.

3. The method of claim 1, wherein the heteroatom-doped Beta zeolite further comprises a molar ratio of $SiO_2$ to $Al_2O_3$ of greater than 8.

4. The method of claim 1, wherein the group VIII or VIB metal is Pt.

5. The method of claim 1, wherein the catalyst comprises 0.1 wt. % to 1.5 wt. % Pt.

6. The method of claim 1, wherein the hydrocarbon feedstock contacts the catalyst under one or more isomerization conditions.

7. The method of claim/wherein the one or more isomerization conditions comprise a temperature from 100° C. to 450° C., a pressure from 0 psig to 1000 psig, a WHSV from 0.1 $hr^{-1}$ to 10 $hr^{-1}$, and/or a hydrogen/hydrocarbon mole ratio from about 0.1 to about 100.

8. The method of claim 1, wherein the hydrocarbon feedstock comprises n-pentane, n-hexane, and/or n-heptane.

9. The method of claim 8, wherein the hydrocarbon feedstock further comprises a naphthene and/or one or more aromatic compounds.

10. A method for hydroisomerization of a hydrocarbon feedstock comprising contacting the hydrocarbon feedstock with hydrogen and a catalyst to yield a hydrocarbon product having an increase in branched hydrocarbons relative to the hydrocarbon feedstock, wherein the catalyst comprises a heteroatom-doped Beta zeolite having a trivalent cation as a framework metal oxide, an extra-framework species comprised of cerium and from 0.01 to 1.5 wt. % of a group VIII or VIB metal, or a combination thereof, the hydrocarbon feedstock comprises $C_5$-$C_{30}$ normal paraffins and/or $C_5$-$C_{30}$ monobranched paraffins and the heteroatom-doped Beta zeolite selectively converts $C_5$, $C_6$ and $C_7$ in the hydrocarbon feedstock.

* * * * *